United States Patent
Goslin et al.

(10) Patent No.: US 10,397,350 B2
(45) Date of Patent: Aug. 27, 2019

(54) TRACKING WEARABLES OR OTHER DEVICES FOR EMOJI STORIES

(71) Applicant: Disney Enterprises, Inc., Burbank, CA (US)

(72) Inventors: Michael P. Goslin, Sherman Oaks, CA (US); Katherine M. Bassett, Pasadena, CA (US)

(73) Assignee: Disney Enterprises, Inc., Burbank, CA (US)

( * ) Notice: Subject to any disclaimer, the term of this patent is extended or adjusted under 35 U.S.C. 154(b) by 135 days.

(21) Appl. No.: 15/716,069

(22) Filed: Sep. 26, 2017

(65) Prior Publication Data
US 2019/0098099 A1    Mar. 28, 2019

(51) Int. Cl.
| | |
|---|---|
| G06F 3/00 | (2006.01) |
| H04L 29/08 | (2006.01) |
| G06F 3/01 | (2006.01) |
| G06K 9/00 | (2006.01) |
| G06Q 50/00 | (2012.01) |
| H04L 12/58 | (2006.01) |
| A61B 5/0205 | (2006.01) |
| A61B 5/16 | (2006.01) |

(52) U.S. Cl.
CPC .............. *H04L 67/22* (2013.01); *G06F 3/011* (2013.01); *G06K 9/00892* (2013.01); *G06Q 50/01* (2013.01); *H04L 51/02* (2013.01); *A61B 5/0205* (2013.01); *A61B 5/165* (2013.01)

(58) Field of Classification Search
None
See application file for complete search history.

(56) References Cited

U.S. PATENT DOCUMENTS

| | | | | |
|---|---|---|---|---|
| 2016/0270717 | A1* | 9/2016 | Luna | G06F 19/3481 |
| 2018/0207479 | A1* | 7/2018 | Brown | G08B 21/182 |
| 2018/0256095 | A1* | 9/2018 | Arnold | A61B 5/486 |

OTHER PUBLICATIONS

Caetano M. Ranieri at al., An Emotion-Based Interaction Strategy to Improve Human-Robot Interaction, Oct. 2016, IEEE, pp. 31-36 (Year: 2016).*
Sandra Costa et al., A Pilot Studay using Imitation and Storytelling Scenarios, Oct. 2014, IEEE International Conferences on Development and Learning, pp. 299-304 (Year: 2014).*

* cited by examiner

*Primary Examiner* — Tam T Tran
(74) *Attorney, Agent, or Firm* — Patterson + Sheridan, LLP

(57) ABSTRACT

Systems, methods and computer program products to perform an operation comprising determining, based on interaction data stored in a first profile, that a first toy device communicated with a second toy device, wherein the first and second toy devices are within a predefined distance during the communication, determining at least one emotion reflected in an emotion data of the first profile, determining at least one activity reflected in an activity data of the first profile, and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

20 Claims, 10 Drawing Sheets

TRACKING WEARABLES OR OTHER DEVICES FOR EMOJI STORIES

BACKGROUND

Field of the Disclosure

Embodiments disclosed herein relate to user interaction via wearable devices, toy devices, and other types of user devices. More specifically, embodiments disclosed herein relate to tracking social wellness through wearables or other devices for generating emoji stories.

Description of the Related Art

Wearable devices (and mobile devices) can monitor physical activities of a user, such as a number of steps taken by the user in a day. However, wearable devices are limited to tracking specific, limited physical activities and/or attributes of users. As such, wearable devices have not monitored other important aspects of user behavior and activities, such as emotions and/or social interactions.

SUMMARY

According to one embodiment of the present disclosure, a method comprises determining, based on interaction data stored in a first profile, that a first toy device communicated with a second toy device, wherein the first and second toy devices are within a predefined distance during the communication, determining at least one emotion reflected in an emotion data of the first profile, determining at least one activity reflected in an activity data of the first profile, and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

In another embodiment, a system comprises a processor and a memory containing a program which when executed by the processor performs an operation comprising determining, based on interaction data stored in a first profile, that a first toy device communicated with a second toy device, wherein the first and second toy devices are within a predefined distance during the communication, determining at least one emotion reflected in an emotion data of the first profile, determining at least one activity reflected in an activity data of the first profile, and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

In another embodiment, a computer program product comprises a non-transitory computer readable medium storing instructions, which, when executed by a processor, performs an operation comprising determining, based on interaction data stored in a first profile, that a first toy device communicated with a second toy device, wherein the first and second toy devices are within a predefined distance during the communication, determining at least one emotion reflected in an emotion data of the first profile, determining at least one activity reflected in an activity data of the first profile, and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

BRIEF DESCRIPTION OF THE DRAWINGS

So that the manner in which the above recited aspects are attained and can be understood in detail, a more particular description of embodiments of the disclosure, briefly summarized above, may be had by reference to the appended drawings.

It is to be noted, however, that the appended drawings illustrate only typical embodiments of this disclosure and are therefore not to be considered limiting of its scope, for the disclosure may admit to other equally effective embodiments.

DETAILED DESCRIPTION

Embodiments disclosed herein track user emotions, travel, social interactions, physical activity, and mental health activities using one or more of wearable devices, toy devices, and mobile devices. For example, toy devices may be configured to determine when two or more of the toy devices are within a specified distance of each other, e.g., using radio communications. When two of the devices are within the specified distance, the toy devices (and/or other devices of the users) may monitor attributes of the interaction, such as a duration of the interaction, a location where the interaction occurs, the users involved in the interaction, any activities performed by the users during the interaction, and emotions expressed by the users before, during, and after the interaction. Doing so allows the toy devices (and/or other devices) to encourage social interaction, travel, and other activities to promote user wellness.

More generally, the toy devices and/or other devices are configured to monitor physical activities, travel engaged in by the users, social activities engaged in by the users, and non-physical (also referred to as wellness) activities engaged in by the users. Similarly, the user may manually enter indications of physical activities, travel, social activities, and wellness activities engaged in. Based on the monitoring and/or user-specified data, embodiments disclosed herein may compute one or more scores for the user. For example, if a user has not engaged in any physical activity or met with friends during the morning, embodiments disclosed herein may compute one or more scores reflecting the levels of physical activity and social interaction engaged in by the user. Based on the scores, embodiments disclosed herein may output notifications to the user (e.g., via the toy devices, wearable devices, mobile devices, etc.) to encourage the user to engage in physical activity with a friend.

Furthermore, embodiments disclosed herein may generate a "story" for a user, reflecting the different emotions, activities, and other aspects of the user's day. In some embodiments, the story includes emoji of known characters (e.g., cartoon characters, toy characters, etc.). Furthermore, the story may follow plot elements from movies, cartoons, and other programs the characters have appeared in. Doing so generates a story that incorporates the user's day with the characters and plot elements of their favorite characters and stories.

Figure 1:
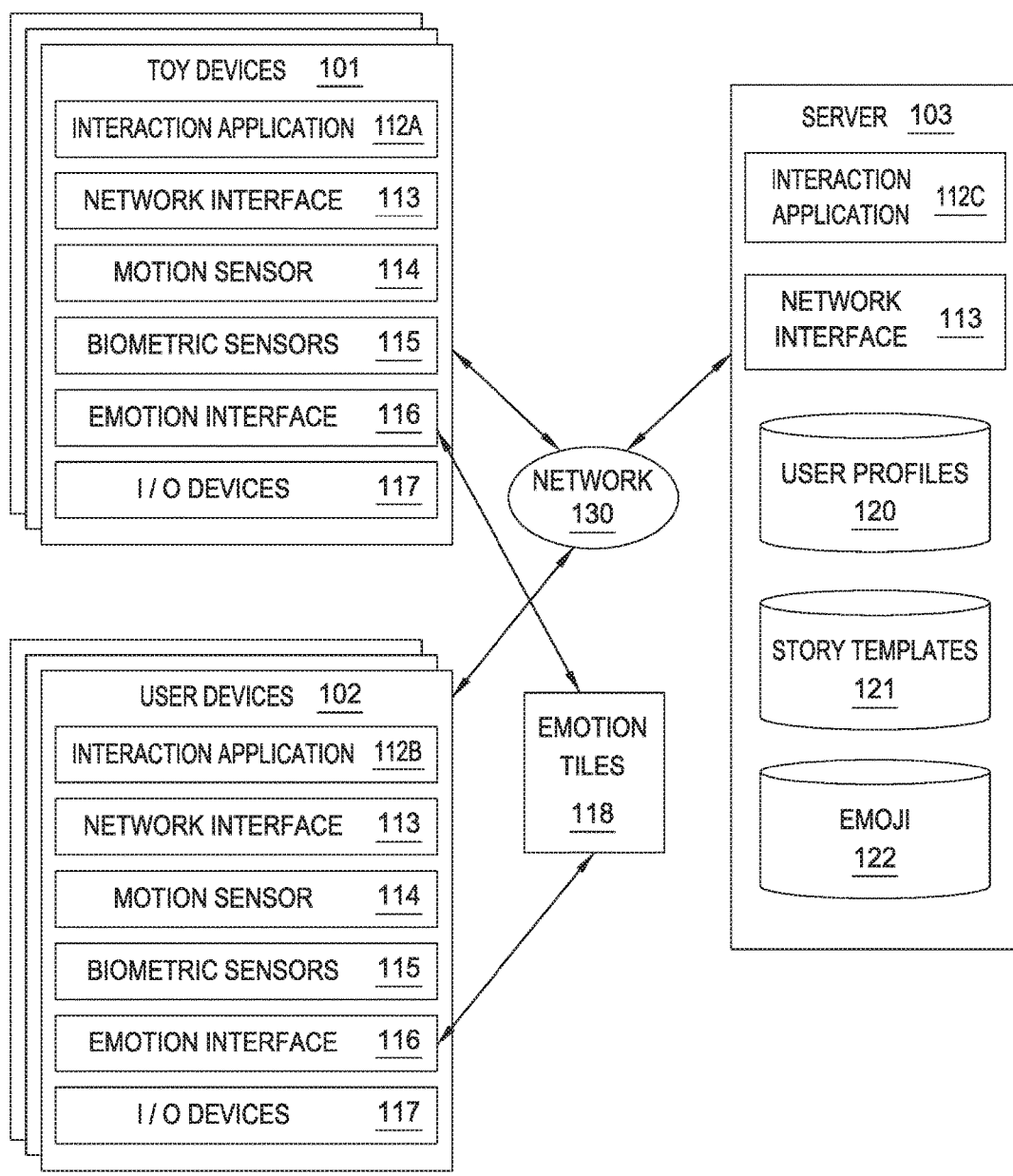
FIG. 1 illustrates a system which tracks social wellness through wearable or other devices to generate emoji stories, according to one embodiment.

FIG. 1 illustrates a system 100 which tracks social wellness through wearable or other devices to generate emoji stories, according to one embodiment. As shown, the system 100 includes a plurality of toy devices 101, a plurality of user devices 102, and at least one server 103 communicably coupled by a network 130. As shown, the toy devices 101 include an instance of an interaction application 112A, a network interface 113, a motion sensor 114, one or more biometric sensors 115, an emotion interface 116, and one or more input/output (I/O) devices 117. The toy devices 101 are representative of any type of toy, such as plush toys, action figures, dolls, robots, and the like. The network interface 113 facilitates communication between the toy device 101 and other toy devices 101, user devices 102, and the server 103. Example network interfaces 113 include wireless local area network (WLAN) interfaces, Bluetooth® interfaces, radio frequency interfaces that allow direct communications between two toy devices 102, and the like. The motion sensor 114 is representative of any hardware module which can detect motion, such as an accelerometer, gyroscope, global positioning system (GPS) radios, and some network interfaces 113. The biometric sensors 115 are representative of any type of sensor which monitors a biometric attribute of the user, such as heartrate sensors, blood pressure sensors, temperature sensors, perspiration sensors, and the like.

The emotion interface 116 is representative of software modules configured to determine user emotions and/or hardware modules configured to interface with the hardware emotion tiles 118. For example, the emotion interface 116 may include emotion detection algorithms configured to detect emotions in captured images of users, and algorithms configured to determine emotions based on the data collected by the biometric sensors 115. The emotion tiles 118 are representative of hardware elements that can plug into the toy devices 101 (and/or the user devices 102), where each emotion tile 118 is associated with a predefined emotion. For example, a "happiness" emotion tile 118 may be a physical tile with a smiling face drawn on it, which, when plugged in to the emotion interface 116, allows the user to convey that they are currently happy. As another example, multiple emotion tiles 118 may be pre-built into the emotion interface 116 of the toy devices 101 and/or user devices 102. For example, a wearable device 102 (e.g., a wristband) may be manufactured to include a happiness emotion tile 118, a sadness emotion tile 118, and an excitement emotion tile 118 integrated into a respective emotion interface 116, which, when selected, allows the user to convey that they are experiencing the corresponding emotion.

As shown, each of the user devices 102 include a respective instance of the interaction application 112B, a network interface 113, one or more biometric sensors 115, the emotion interface 116, and the one or more input/output (I/O) devices 117. The user devices 102 are representative of any type of mobile device, such as a smartphone, wearable computing device, smart watch, fitness tracker, tablet computer, portable game console, and the like. As shown, the server 103 includes an instance 112C of the interaction application, a network interface 113, and data stores of user profiles 120, story templates 121, and emoji 122. The user profiles 120 store profile data for a plurality of different users, including user attributes (e.g., emotions, locations visited, activities engaged in, achievements, relationships, friendships between toy devices 101, etc.). The story templates 121 define plot elements used to generate emoji stories for a user. For example, the story templates 121 may include plot elements of different movies, books, or other videos, that can be adapted to the different experiences of a user on a given day. The emoji 122 stores a plurality of different emoji, which are digital images or icons that may express an idea, emotion, or concept. While emoji are used as a reference example herein, the disclosure the disclosure is not limited to emoji or other specific types of digital images or icons. Instead, the disclosure is equally applicable to any type of graphical object that expresses an idea, emotion, or concept. Although not pictured in FIG. 1 for the sake of clarity, in at least one embodiment, the user devices 102 include an instance of the user profiles 120 for associated users, an instance of the story templates 121, and an instance of the emoji 122.

The interaction application 112 (which includes instances 112A, 112B, and 112C) is logic configured to track the emotions of an associated user, monitor locations visited by the user, identify social interactions between two or more users (and their corresponding toy devices 101 and/or user devices 102), monitor physical activity of the user, and monitor wellness activities (e.g., sleep, meditation, relaxation, etc.) engaged in by the user. The interaction application 112 is further configured to compute scores for the user, where the scores include one or more of a travel score, a physical activity score, a social interaction score, and a wellness score. The scores may also include composite scores based on two or more of the travel score, physical activity score, social interaction score, and wellness score. The interaction application 112 may then compare the computed scores to an applicable threshold, and generate notifications or other indications which may be outputted to the user to encourage the user to engage in activities that would increase the corresponding score.

For example, as previously stated, the toy devices 101 are configured to detect other toy devices 101 via the respective network interfaces 113. When the network interface 113 of a toy device 101 identifies another toy device 102, the interaction application 112A may transmit an indication of the encounter to the instance of the interaction application 112B on a paired user device 102 (e.g., a smartphone). If the toy device 101 of a first user does not come in contact with any other toy devices 101 for a predefined amount of time, the instance of the interaction application 112B does not receive an indication of an encounter from the toy device 101. The instance of the interaction application 112B on the paired user device 102 (and/or the interaction application 112A on the toy device 101) may then compute a social interaction score for the first user, which does not exceed a corresponding threshold (because the user has not interacted with other users of toy devices 101). The instance of the interaction application 112B on the paired user device 102 may then output an notification via one of the I/O devices 117 (e.g., a speaker or display device) encouraging the user to interact with friends.

Furthermore, the interaction application 112 is configured to generate an emoji story for the user. The emoji story may be generated based on any number of attributes of the user's day. The attributes include, but are not limited to, interaction data reflecting one or more of the number of social interactions (detected by the toy devices 101 and/or user devices 102) engaged in by the user, interaction data reflecting a duration of detected social interactions for the user, emotion data reflecting emotions experienced/expressed by the user, emotion data reflecting detected emotions expressed by the user, biometric data of the user captured by the biometric sensors 115, activity data reflecting activities engaged in by the user, and the scores computed for the user. In at least one embodiment, the emoji story includes one or more emoji 122, and is based on a story template 121. For example, if the user adds an emotion tile 118 to a wearable device 102 indicating the user is excited after getting a perfect exam grade, the emoji story for the user's day may reflect the user's excitement and a congratulatory message for the user's achievement.

Figure 2A:
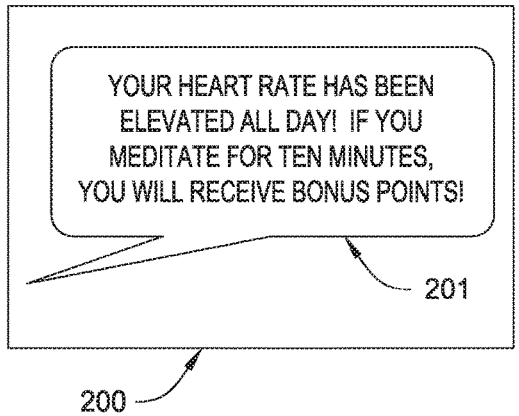
FIGS. 2A-2D illustrate examples of user interaction based on tracking social wellness, according to various embodiments.

FIG. 2A depicts an example display device 200 which outputs an example of user interaction based on social wellness tracking, according to one embodiment. In at least one embodiment, the display device 200 is a component of a user device 102 (e.g., a smartphone, tablet, smart watch, etc.). As shown, the display 200 outputs an example graphical user interface (GUI) element 201. The GUI element 201 notifies the user that their heart rate is elevated, and offers the user a reward for engaging in meditation. As previously stated, the biometric sensors 115 of the toy device 101 and/or user devices 102 may monitor the heart rate of the user, and determine that the heart rate exceeds a threshold. Similarly, the interaction application 112 may compute a wellness score for the user based on the amount of wellness activities (e.g., meditation) the user has engaged in that day. If the data captured by the biometric sensors 115 does not indicate the user has engaged in meditation, the wellness score may not exceed a wellness threshold. As such, the instance of the interaction application 112B on the user device 102 may output the notification 201 to the user via the display 200.

If the user engages in meditation, the interaction application 112B may update the user's profile 120 to reflect an award of bonus points (e.g., for a game, social networking status, etc.). For example, if the user specifies they are engaging in meditation (e.g., via an emotion tile 118, or other user input), the bonus points may be awarded. Similarly, the biometric sensors 115 may detect a lower heart rate for the user, less perspiration on the user's skin, and a cooler body temperature. The interaction application 112A/B may then determine that the user is engaged in meditation, and may monitor the duration of the meditation session. If the duration exceeds the specified time threshold (e.g., 10 minutes), the bonus points are added to the user profile 120.

Figure 2B:
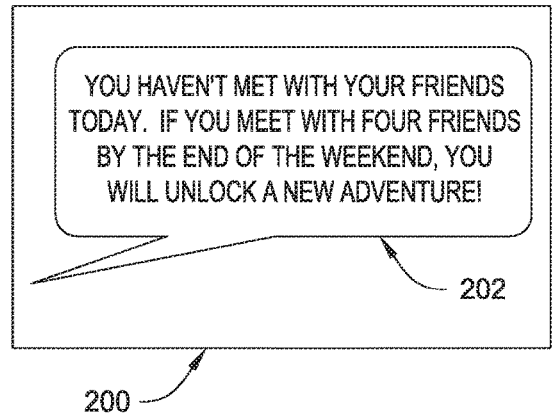

FIG. 2B depicts an example notification 202 generated based on monitoring social interactions of a user via a toy device 101, according to one embodiment. As previously stated, the toy devices 101 are configured to identify similar toy devices 101 via the network interface 113. If a first toy device 101 detects a second toy device 101 within a predefined distance, the first and second toy devices 101 may generate an indication of the encounter, and send the indication of the encounter to associated user devices 102. In response, the users may be prompted, via the user devices 102, to accept "friendship" of the first and second toy devices 101. If the users accept the "friendship" request, an indication of the friendship is stored in the user profiles 120 of the users.

Generally, the interaction application 112 monitors such interaction between toy devices 101, including number of encounters with other toy devices 101, a duration of the encounter, whether a friendship relationship exists between the toy devices 101, emotions expressed by the users during the encounter, and the like. The interaction application 112 may then compute a social interaction score for the user. In the embodiment depicted in FIG. 2B, the user has yet to interact with any friends on a given day. As such, the interaction application 112 generates a social interaction score that does not exceed a social interaction threshold. The interaction application 112 may then generate the notification 202, indicating that the user will unlock an adventure in a video game if the user meets with four friends (e.g., having toy devices 101) by the end of the weekend. Again, the interaction application 112 may monitor the interactions of the user's toy device 101 with other toy devices 101. If the toy device of the user comes within proximity of four toy devices 101 by the end of the weekend, the interaction application 112 unlocks the adventure for the user, and updates the user profile 120 accordingly.

Figure 2C:
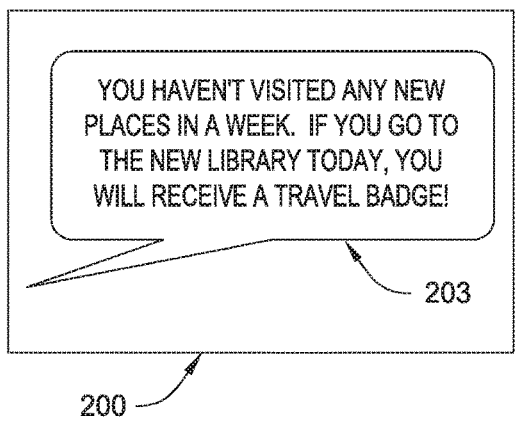

FIG. 2C depicts an example notification 203 generated based on monitoring travel of a user, according to one embodiment. As previously stated, the network interfaces 113 and/or motion sensors 114 of the toy devices 101 and/or user devices 102 are configured to monitor locations visited by the associated user. The interaction application 112 may then receive the data indicating the locations visited by the user, and compute a travel score for the user. The travel score may be based on one or more of the number of places visited, the types of places visited, whether new places were visited by the user, and the like. If the user does not frequently travel, or has not traveled in some time, the interaction application 112 generates a travel score that does not exceed a threshold. As such, the interaction application 112 generates the notification 203, which encourages the user to visit the new library in town in exchange for a travel badge. If location data generated by the toy devices 101 and/or user devices 102 of the user indicates that the user visited the new library, the interaction application 112 updates the user profile 120 to reflect the awarding of the travel badge.

Figure 2D:
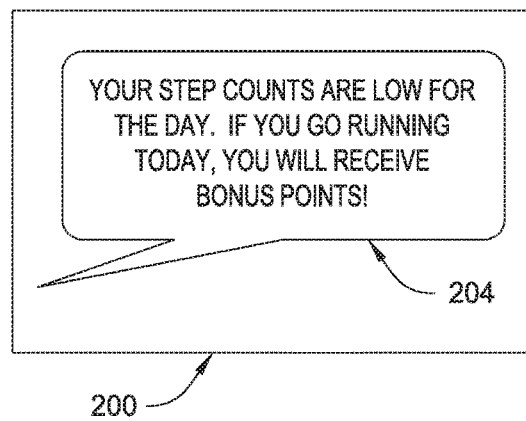

FIG. 2D depicts an example notification 204 generated based on monitoring physical activity of a user, according to one embodiment. As previously stated, the motion sensors 114 of the toy devices 101 and/or user devices 102 are configured to monitor movement of the user. For example, the motion sensors 114 may determine, based on collected motion data, that the user has taken 1,000 steps in a given day. The interaction application 112 may then compute a physical activity score for the user, which, because of the low step count, does not exceed a physical activity threshold. In response, the interaction application 112 generates and outputs the notification 204, which encourages the user to go running to receive bonus points. In some embodiments, the user may enter an indication that the user went running via a GUI (not pictured) of the interaction application 112. In other embodiments, the data collected by the motion sensors of the toy devices 101 and/or user devices 102 may reflect an increased step count for the user (e.g., 12,000 steps). As such, the interaction application 112 may determine, based on the increased step count, that the user went running, and update the user profile 120 of the user to reflect the addition of bonus points to their account. Although depicted as visual notifications, the notifications 201-204 may be audio notifications in some embodiments.

Figure 3:
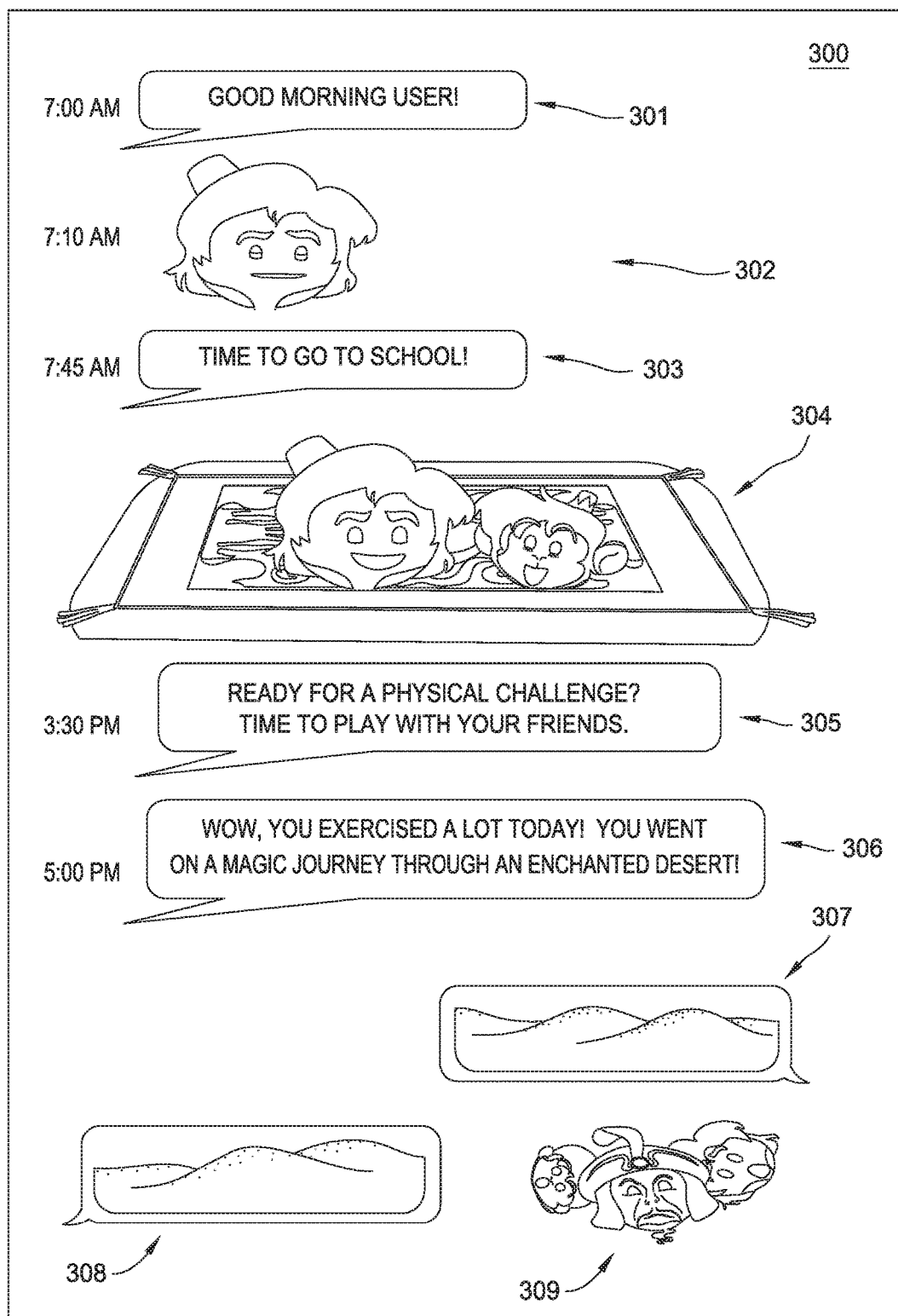
FIG. 3 illustrates an example emoji story, according to one embodiment.

FIG. 3 illustrates an example emoji story 300, according to one embodiment. As shown, the emoji story 300 includes elements 301-309. As previously stated, the emoji story 300 is generated based on the monitoring of the toy devices 101 and/or user devices 102 of the user, emotions of the user, as well as any scores computed for the user by the interaction application 112. As shown, the element 301 is a text-based wake-up message reflecting when the user wakes up (e.g., based on motion data from the motion sensors 114, biometric data from the biometric sensors 113, etc.). The element 302 is an emoji 122 that is expressing the emotion of sleepiness, reflecting that the user is sleepy after waking up in the morning. The emoji 122 may the emoji of a movie character. The emoji 122 expressing sleepiness may be outputted based on a determination that the user was sleepy when waking up. For example, the user may select a sleepiness emotion tile 118 indicating they are sleepy. The element 303 is a text-based message that indicates the user went to school, while the element 304 includes two example emoji 122 that are taking a magic carpet ride. Doing so gives the user the impression they rode a magic carpet to school, and incorporates a plot element from a story template 121 associated with a movie that involves magic carpet rides.

The element 305 is a text-based message that indicates the user was playing with friends (e.g., based on the detection of nearby toy devices 101 by the toy device 101 of the user). Element 306 reflects that the user engaged in physical activity (e.g., steps and/or movement detected by the motion sensors 114, elevated heart rated and/or perspiration detected by the biometric sensors 115, etc.). Furthermore, as shown, the text of the element 306 is tailored to the user based on the story template 121 of the movie, which includes elements of a desert. Similarly, as shown, elements 307-308 depict the desert, while element 309 depicts emoji 122 of characters depicted in the movie. Again, the emoji 122 may be characters of the movie. Although not depicted in FIG. 3, the emoji story 300 may further include audio tones, songs, tactile feedback, and the like. Furthermore, as shown, one or more elements 301-309 may include an associated timestamp indicating at which time of day the corresponding events occurred.

Figure 4:
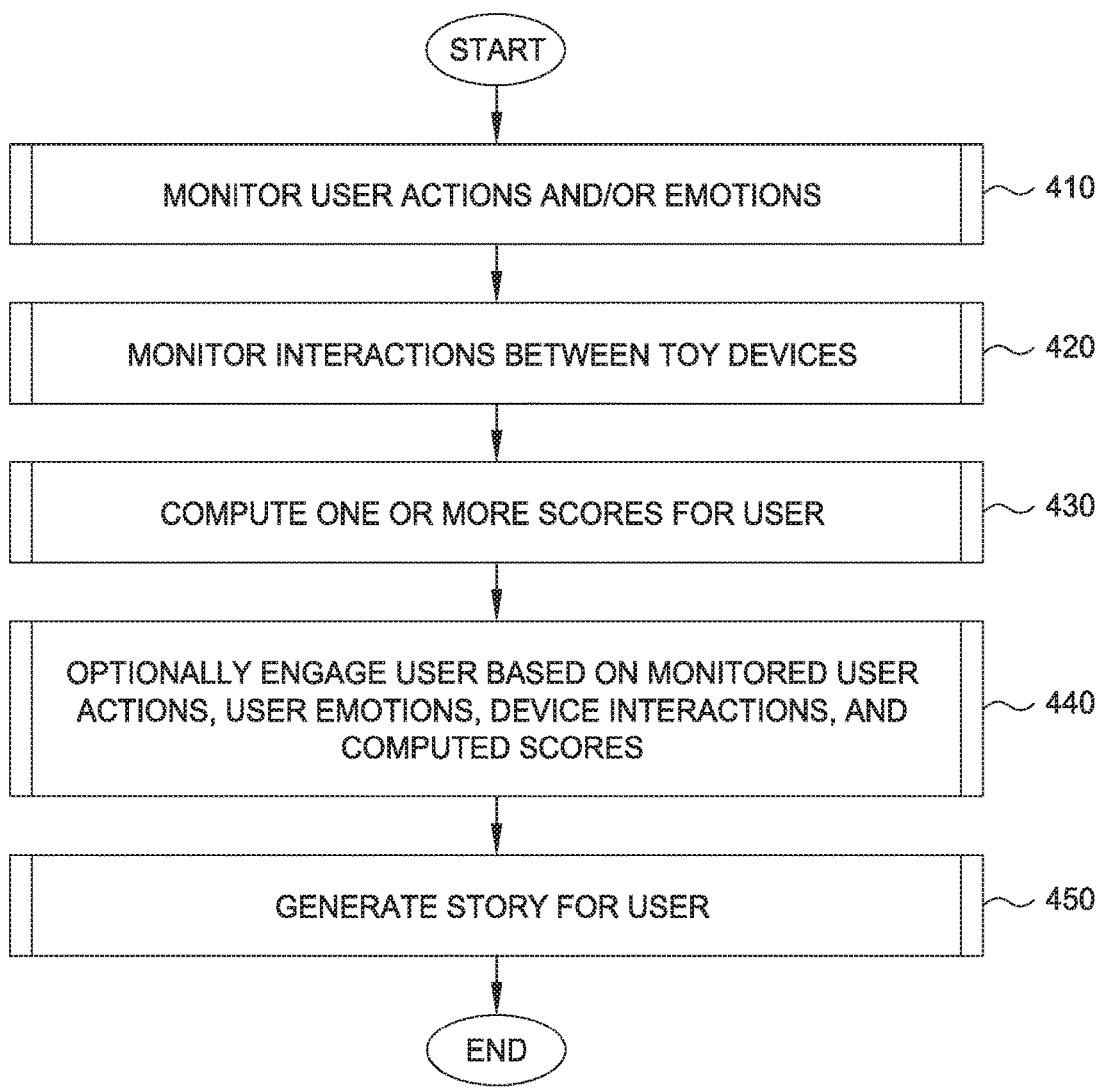
FIG. 4 is a flow chart illustrating an example method to track social wellness through wearable or other devices to generate emoji stories, according to one embodiment.

FIG. 4 is a flow chart illustrating an example method 400 to track social wellness through wearable or other devices to generate emoji stories, according to one embodiment. As shown, the method 400 begins at block 410 where the actions and/or emotions of a user are monitored via the toy devices 101 and/or the user devices 102. Generally, the monitoring includes, without limitation, physical activities (e.g., steps, exercise, playing sports, etc.), travel, wellness activities (e.g., sleep, meditation, rest, etc.), social interactions, observed emotions, user-specified emotions, biometric data, and the like. At block 420, the interactions between two or more toy devices 101 are monitored. As previously stated, the toy devices 101 are able to detect other toy devices 101 in proximity. Doing so allows the toy devices 101 and/or associated user devices 102 to collect data regarding the interactions, such as duration, emotions expressed by the users, locations where the interactions took place, and the like. At block 430, the interaction application 112 computes one or more scores for the user. For example, the interaction application 112 may compute a travel score, a physical activity score, a social interaction score, and a wellness score for the user at periodic intervals.

At block 440, the interaction application 112 optionally engages the user based on one or more of the monitored user actions, user emotions, device interactions, and the scores computed for the user. For example, if the interaction application 112 determines, based on data from the biometric sensors 115, that the user is not getting enough sleep, the interaction application 112 may compute a wellness score for the user that falls below a wellness threshold. The interaction application 112 may then output a notification to the user via one or more user devices 102 to encourage the user to sleep, rest, relax, etc. At block 450, the interaction application 112 generates an emoji story for the user. The emoji story may reflect the highlights of the user's day, and may be based on a story template 121, and include emoji 122.

Figure 5:
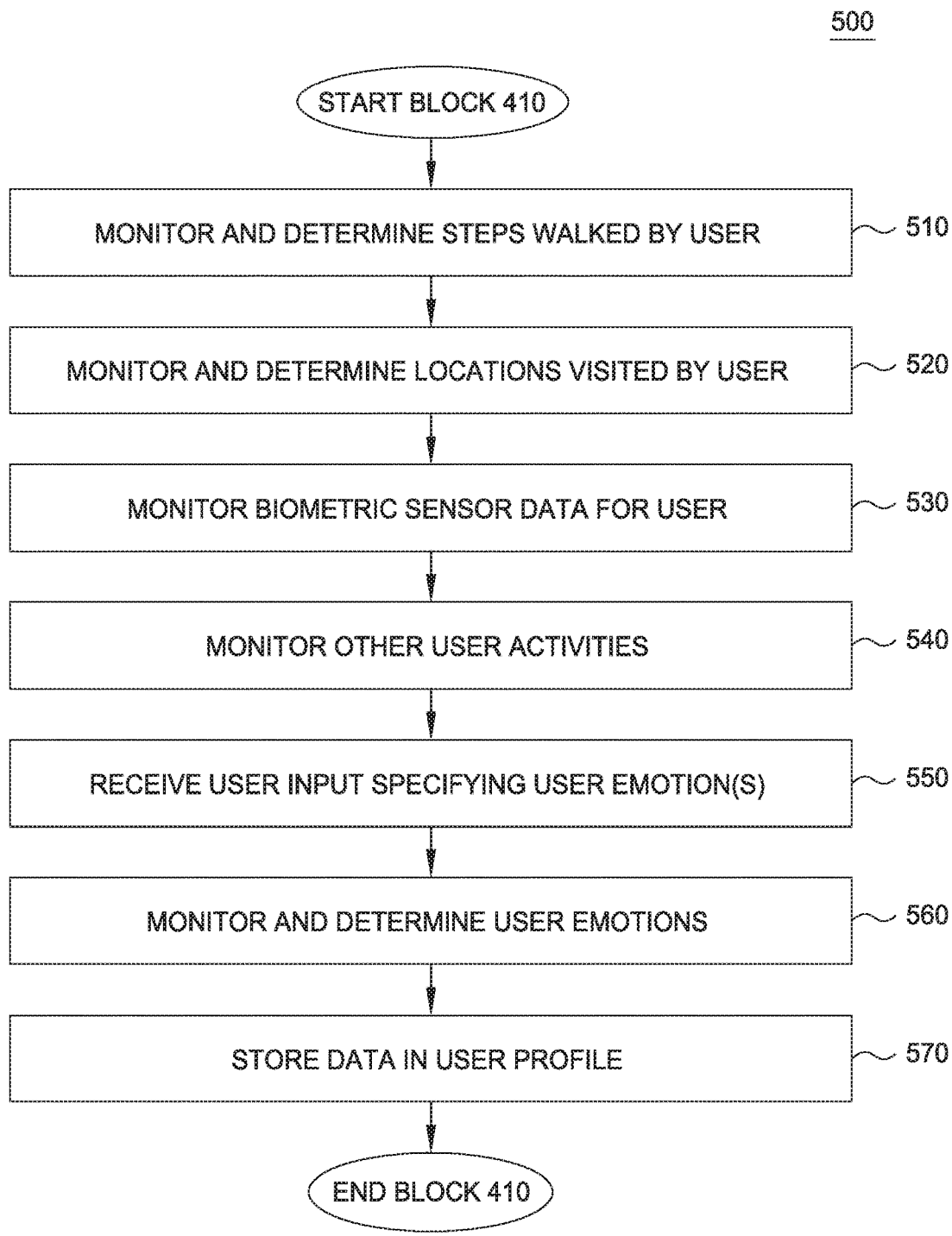
FIG. 5 is a flow chart illustrating an example method to monitor user actions and/or emotions, according to one embodiment.

FIG. 5 is a flow chart illustrating an example method 500 corresponding to block 410 to monitor user actions and/or emotions, according to one embodiment. Generally, the steps of the method 500 may be performed at periodic intervals to monitor user actions and/or emotions. As shown, the method 500 begins at block 510, where the motion sensors 114 of the toy device(s) 101 and/or user device(s) 102 of a user monitor and determine the number of steps walked by a user. At block 520, the toy device(s) 101 and/or user devices 102 of a user monitor and determine the locations visited by the user. For example, the network module 113 of the devices 101, 102 may connect to a wireless access point at an airport, and the interaction application 112 may determine that the user has visited the airport and its corresponding region, city, state, etc. Similarly, the motion sensors 114 may include a GPS module, which provides data to the interaction application 112. The interaction application 112 may then determine corresponding places, business, establishments, theme parks, cities, states, countries, etc. visited by the user.

At block 530, the biometric sensors 115 of the toy device(s) 101 and/or user device(s) 102 monitor the biometric data of the associated user. For example, the heart rate, body temperature, skin temperature, perspiration rates, etc. of the user may be monitored by the biometric sensors 115. At block 540, the toy device(s) 101 and/or user device(s) 102 monitor the other activities engaged in by a user to collect activity data for the respective user. The other activities generally include physical activities, wellness activities (e.g., sleep, meditation, and rest), attending school, and any other type of activity. At block 550, the toy device(s) 101 and/or user device(s) 102 receive user input specifying one or more emotions experienced by the user. For example, the user may provide input to the emotion interface 116 specifying they are happy, sad, etc. Similarly, the user may activate an emotion tile 118, or insert an emotion tile 118 into a toy device 101 and/or user device 102 to indicate the corresponding emotion. At block 560, the toy device(s) 101 and/or user device(s) 102 monitor and determine emotions of the user. For example, if the biometric data collected by the biometric sensors 115 indicates the user's heart rate and perspiration levels are elevated while the user is studying for an exam, the interaction application 112 may determine that the user is stressed. Similarly, the emotion interface 116 may analyze images of the user using emotion detection algorithms to determine which emotions the face of the user is expressing. At block 570, the data collected and data representing the determinations made at blocks 510-560 is stored in a user profile 120 of each respective user.

Figure 6:
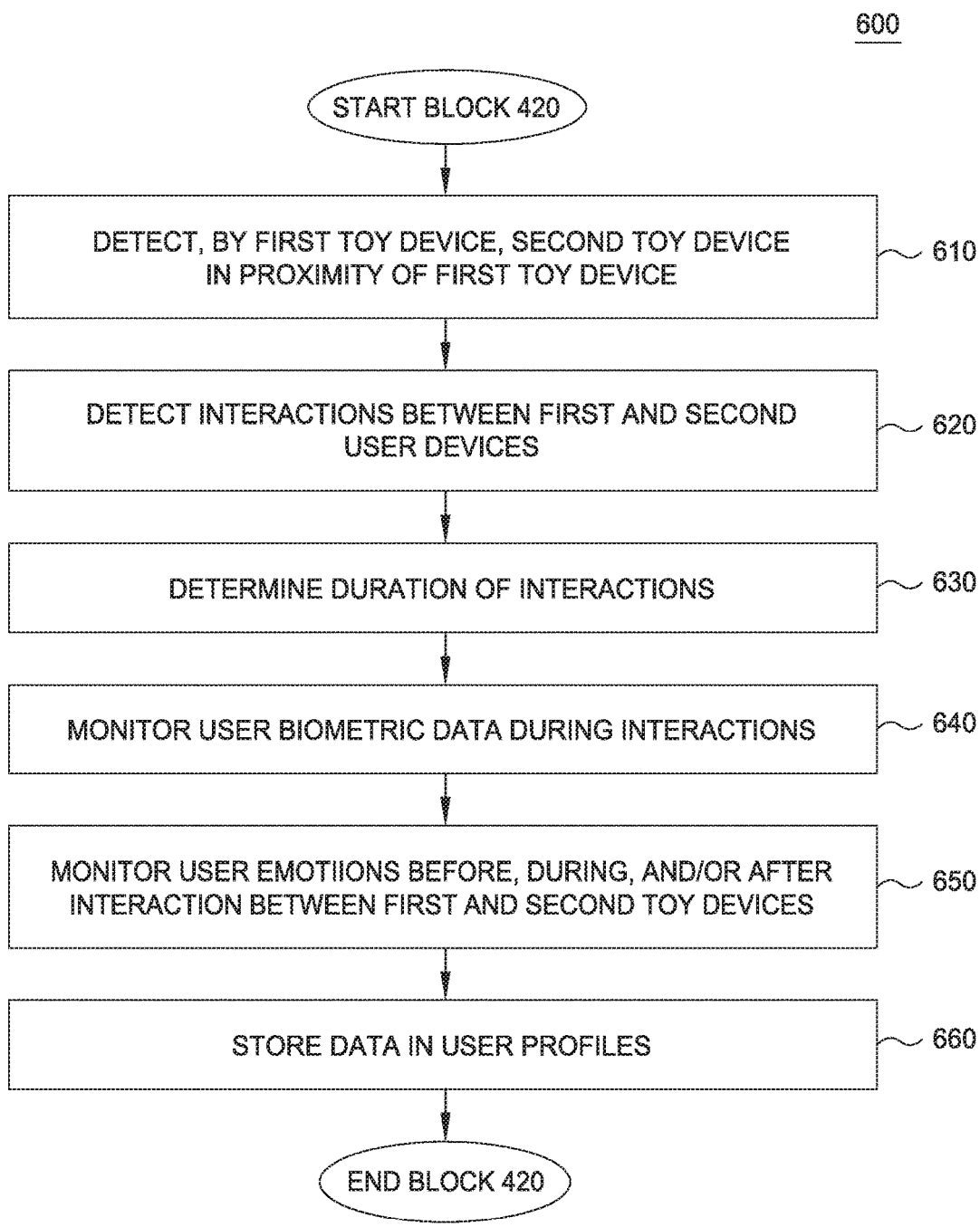
FIG. 6 is a flow chart illustrating an example method to monitor interactions between user devices, according to one embodiment.

FIG. 6 is a flow chart illustrating an example method 600 corresponding to block 420 to monitor interactions between toy devices, according to one embodiment. As shown, the method 600 begins at block 610, where a first toy device 101 of a first user detects at least a second toy device 101 of a second user. As previously stated, the toy devices 101 use the respective network interfaces 113 to detect corresponding toy devices 101 within a predefined distance. Once detected, the respective toy devices 101 may engage in communications, sharing information regarding the respective toy devices 101 (e.g., a hardware identifier of the toy device 101, an indication of the corresponding user of the toy device 101, etc.). At block 620, the interaction applications 112 of a first user device 102 and a second user device 102, of the first and second users, respectively, detect interactions between the devices 102. For example, the users may send each other messages, images, emoji 122, their daily emoji story, share uniform resource locators (URLs), and the like. Similarly, the users may establish a friendship connection between the toy devices 101 and/or their respective user profiles 120 on a variety of different social networking platforms.

At block 630, the toy devices 101 determine a duration of the interactions between two or more toy devices 101. For example, the first and second toy devices 101 may remain in proximity for one minute, while the first toy device 101 may remain in proximity with a third and fourth toy device 101 for an hour. At block 640, the biometric sensors 115 collect biometric data from the users during the interactions. Doing so allows the interaction application 112 to determine that the users have elevated heart rates and therefore are exercising, playing sports, etc. At block 650, the emotions of the users are monitored before, during, and/or after the interactions between the toy devices 101. Doing so allows the interaction application 112 to detect changes in emotion, as well as associate any detected emotions with the corresponding user(s) engaging in the interaction. At block 660, the user profiles 120 are updated to reflect the data collected and determinations made at blocks 610-650.

Figure 7:
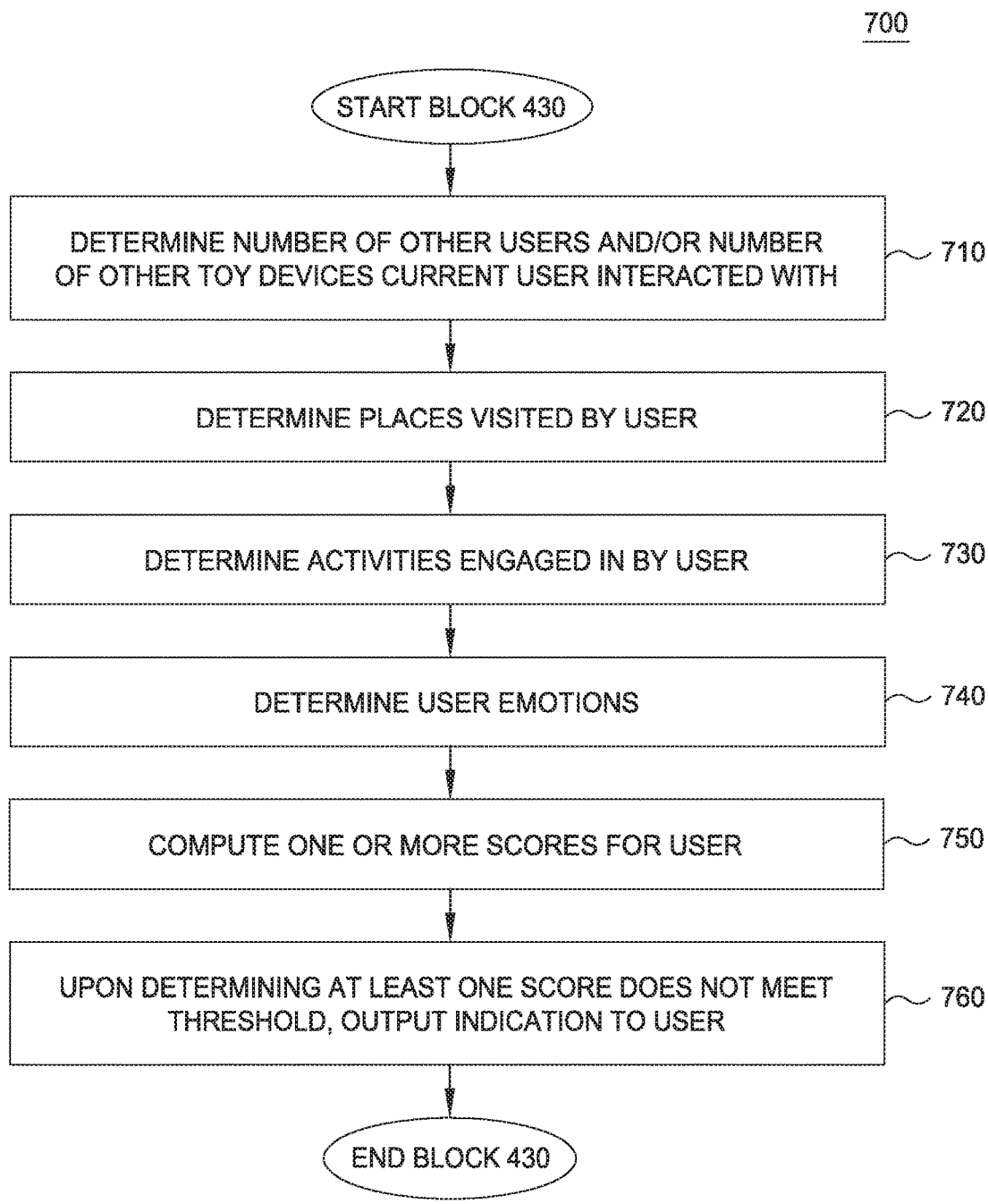
FIG. 7 is a flow chart illustrating an example method to compute one or more scores for a user, according to one embodiment.

FIG. 7 is a flow chart illustrating an example method 700 corresponding to block 430 to compute one or more scores for a user, according to one embodiment. Generally, the interaction application 112 may implement the method 700 for each of a plurality of different users at periodic timing intervals (e.g., hourly, daily, etc.). As shown, the method 700 begins at block 710, where the interaction application 112 determines the number of other users and/or toy devices 101 the current user has interacted with, e.g., based on data stored in the user profile 120 of the current user. At block 720, the interaction application 112 determines the number and types of places the user has visited. As previously stated, the user profile 120 of the user may reflect the locations visited by the user, as determined based on the network interfaces 113 and/or motion sensors 114. At block 730, the interaction application 112 determines the activities engaged in by the user, such as physical activity, steps taken by the user, wellness activities, and the like. Again, the user profile 120 of the user includes indications of detected user activities. At block 740, the interaction application 112 determines the emotions experienced by the user, as reflected in the user profile 120. At block 750, the interaction application 112 computes one or more scores for the user based on the determinations made at blocks 710-750. As previously stated, the interaction application 112 may compute a travel score, a physical activity score, a social interaction score, and a wellness score for the user. At block 760, the interaction application 112 determines that at least one score computed for the user does not meet a corresponding threshold. As such, the interaction application 112 outputs an indication to the user (e.g., to encourage the user to engage in some activity, such as the notifications 201-204 depicted in FIG. 2).

Figure 8:
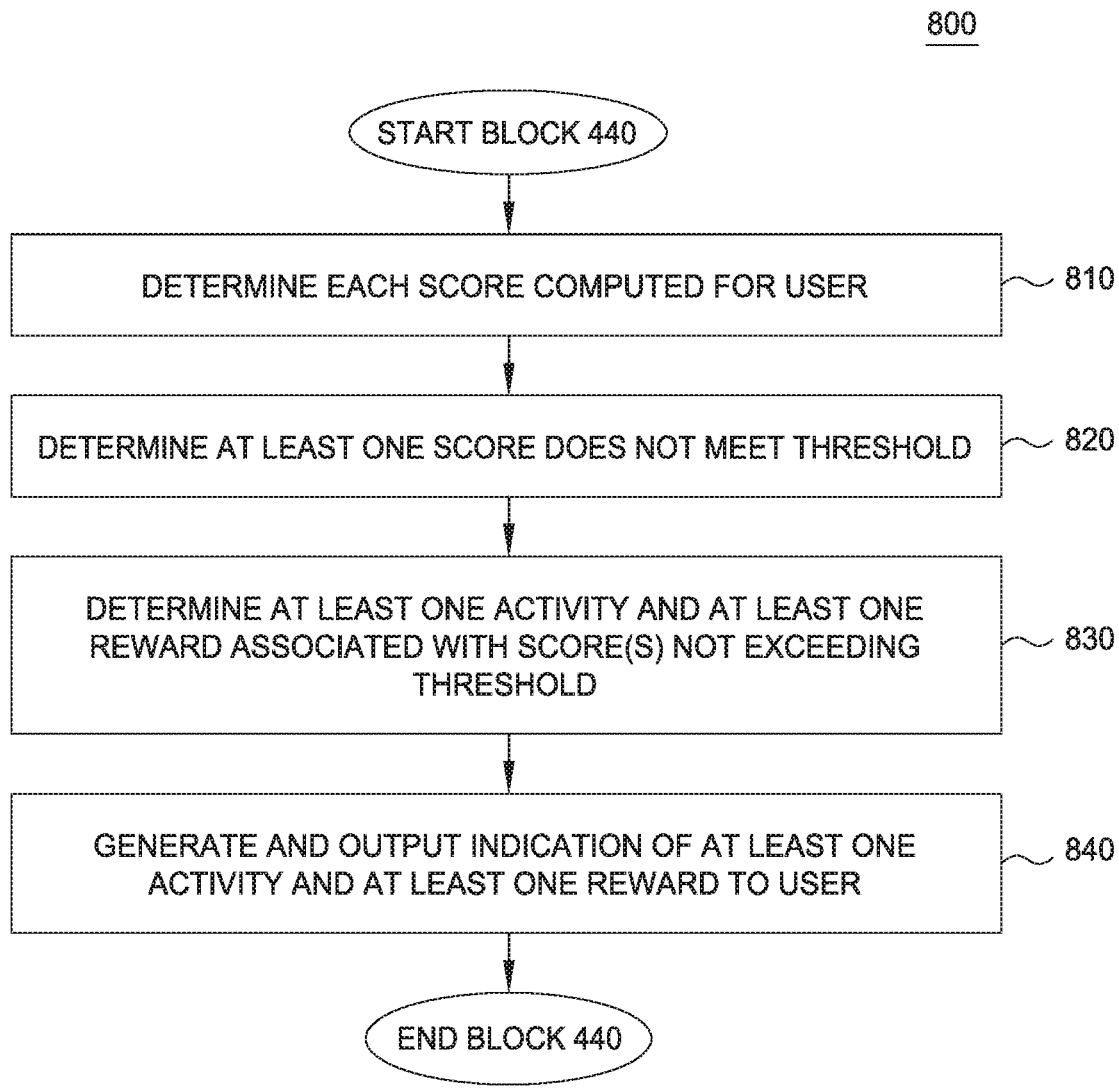
FIG. 8 is a flow chart illustrating an example method to engage users, according to one embodiment.

FIG. 8 is a flow chart illustrating an example method 800 corresponding to block 440 to engage users, according to one embodiment. As shown, the method 800 begins at block 810, where the interaction application 112 determines each score computed for the user at block 750. For example, the scores may include scores of 70, 40, 80, and 90 (on a scale of 100) for physical activity, wellness activities, travel, and social interaction, respectively. At block 820, the interaction application 112 determines that at least one of the computed scores does not meet a corresponding threshold. Continuing with the previous example, the thresholds may be 65, 50, 50, and 75 for physical activity, wellness activities, travel, and social interaction, respectively. As such, the interaction application 112 determines that the wellness activity score does not exceed the threshold. At block 830, the interaction application 112 determines at least one activity and at least one reward associated with the score(s) not exceeding the threshold. For example, the interaction application 112 may encourage a user to or engage a particular type of wellness activity in exchange for a specific reward, where the activity, reward, and computed wellness score are associated based on predefined mappings. At block 840, the interaction application 112 generates and outputs an indication of the at least one activity and at least one reward identified at block 830 to the user (e.g., to encourage the user to engage in some activity, such as the notifications 201-204 depicted in FIG. 2).

Figure 9:
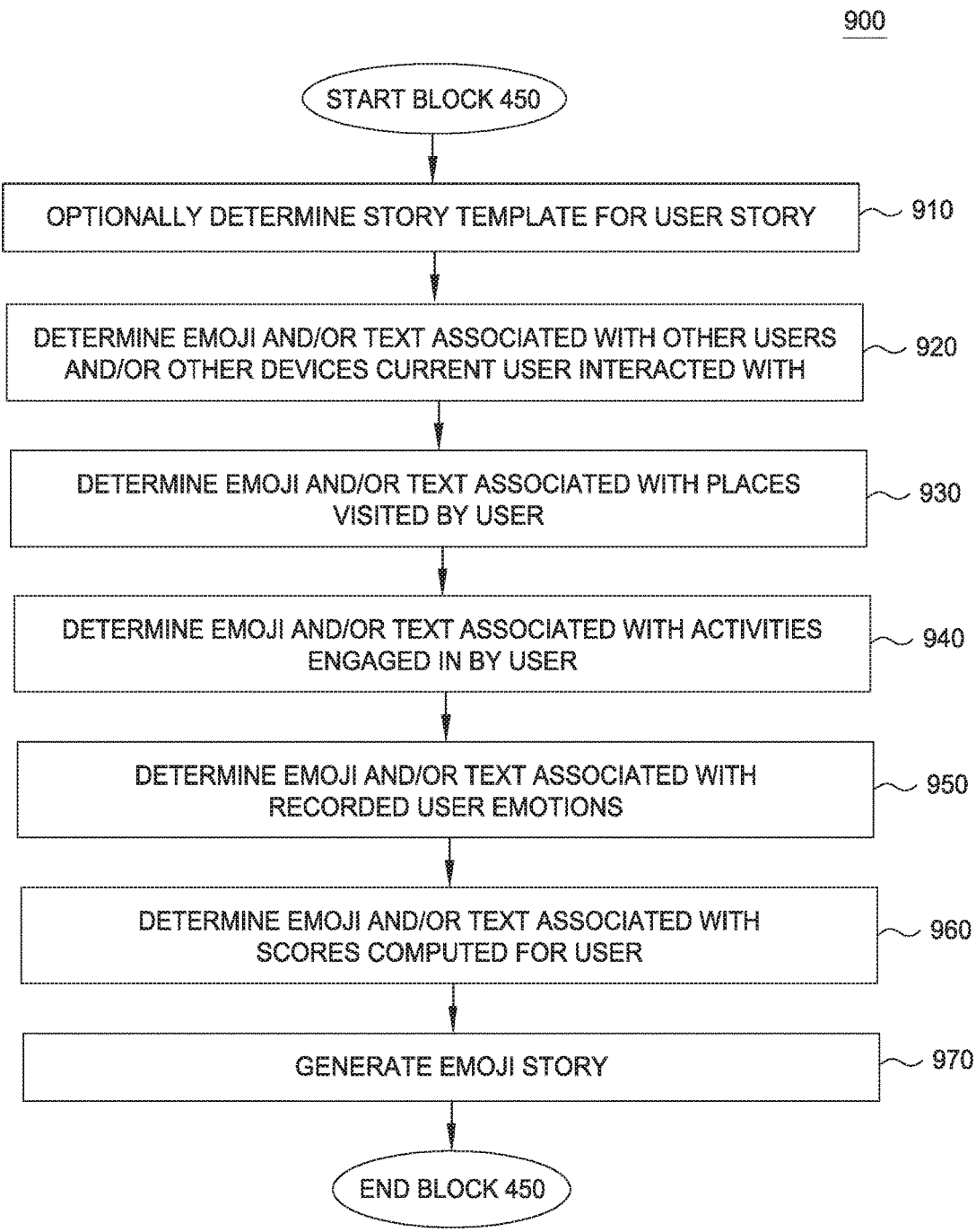
FIG. 9 is a flow chart illustrating an example method to generate an emoji story, according to one embodiment.

FIG. 9 is a flow chart illustrating an example method 900 corresponding to block 450 to generate an emoji story, according to one embodiment. Generally, the interaction application 112 may perform the method 900 for any number of users on a periodic basis (e.g., daily). Additionally, a user may specify a request to generate an emoji story on-demand. As shown, the method 900 begins at block 910, where the interaction application 112 optionally determines a story template for the user. For example, the user profile 120 may include indications of the each user's favorite movies and characters. The interaction application 112 may then identify a story template 121 associated with the movie and/or characters. Similarly, the interaction application 112 may identify the story template 121 based on the detected activities, emotions, and biometric data collected for the user during a given day. For example, if a user played several games of soccer during a day, the interaction application 112 may select a story template 121 having plot elements of a soccer themed movie.

At block 920, the interaction application 112 determines any emoji 122 and/or text associated with the other toy devices 101 and/or users the current user interacted with. For example, each user may have a personalized emoji 122. Similarly, the toy devices 101 each may have a respective emoji 122. As such, the interaction application 112 may use the relevant emoji 122 when generating the emoji story for the user. At block 930, the interaction application 112 determines any emoji 122 and/or text associated with the locations visited by the user. For example, a theme park may have an associated emoji 122. If the user visited the theme park during a given day, the interaction application 112 may include the theme park's emoji 122 in the user's emoji story for that day.

At block 940, the interaction application 112 determines any emoji 122 and/or text associated with the activities engaged in by the user. For example, if the user went to school, the emoji story may include a statement indicating the user went to school. Similarly, if the user played soccer, the emoji story may include an emoji 122 depicting a soccer ball and/or a famous soccer player. At block 950, the interaction application 112 determines any emoji 122 and/or text associated with the emotions recorded for the user in the user profile 120. For example, the emoji 122 may include metadata tagging each emoji with an associated emotion. Therefore, if the user expressed that they were in love, the interaction application 112 may identify emoji 122 having metadata reflecting the emotion of love. At block 960, the interaction application 112 determines any emoji 122 and/or text associated with the scores computed for the user. For example, if the physical activity score computed for the user indicates the user engaged in a significant amount of physical activity, the interaction application 112 may identify emoji 122 associated with physical activity. Similarly, the interaction application 112 may determine congratulatory text associated with different user achievements, etc. At block 970, the interaction application 112 generates an emoji story for the user. The emoji story is generally an ordered depiction of the user's day, with emoji 122, text, and/or other graphics. In at least one embodiment, the interaction application 112 places a limit on the length of the emoji story, and scores each item of the user's day (e.g., social interaction, physical activity, wellness activity, travel activity, emotions, and any other activity engaged in by the user). In such embodiments, the interaction application 112 selects the highest scoring items for inclusion in the emoji story.

Figure 10:
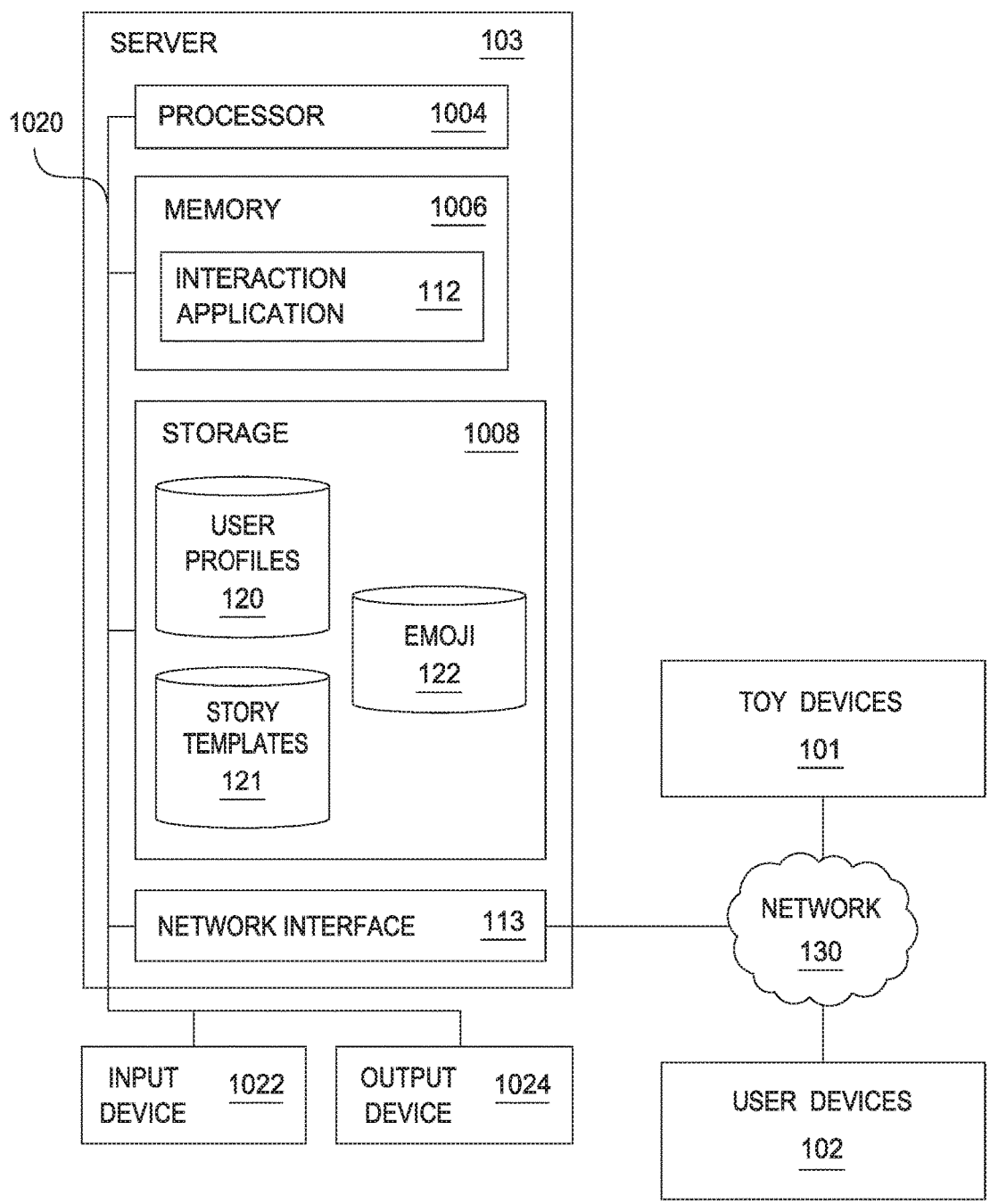
FIG. 10 illustrates a system which tracks social wellness through wearable or other devices to generate emoji stories, according to one embodiment.

FIG. 10 illustrates a system 1000 which tracks social wellness through wearable or other devices to generate emoji stories, according to one embodiment. The networked system 1000 includes the server 103. The server 103 may also be connected to other computers via the network 130. In general, the network 130 may be a telecommunications network and/or a wide area network (WAN). In a particular embodiment, the network 130 is the Internet.

The server 103 generally includes a processor 1004 which obtains instructions and data via a bus 1020 from a memory 1006 and/or a storage 1008. The server 103 may also include one or more network interface devices 113, input devices 1022, and output devices 1024 connected to the bus 1020. The server 103 is generally under the control of an operating system (not shown). Examples of operating systems include the UNIX operating system, versions of the Microsoft Windows operating system, and distributions of the Linux operating system. (UNIX is a registered trademark of The Open Group in the United States and other countries. Microsoft and Windows are trademarks of Microsoft Corporation in the United States, other countries, or both. Linux is a registered trademark of Linus Torvalds in the United States, other countries, or both.) More generally, any operating system supporting the functions disclosed herein may be used. The processor 1004 is a programmable logic device that performs instruction, logic, and mathematical processing, and may be representative of one or more CPUs. The network interface device 113 may be any type of network communications device allowing the server 103 to communicate with other computers via the network 130.

The storage 1008 is representative of hard-disk drives, solid state drives, flash memory devices, optical media and the like. Generally, the storage 1008 stores application programs and data for use by the server 103. In addition, the memory 1006 and the storage 1008 may be considered to include memory physically located elsewhere; for example, on another computer coupled to the server 103 via the bus 1020.

The input device 1022 may be any device for providing input to the server 103. For example, a keyboard and/or a mouse may be used. The input device 1022 represents a wide variety of input devices, including keyboards, mice, controllers, and so on. Furthermore, the input device 1022 may include a set of buttons, switches or other physical device mechanisms for controlling the server 103. The output device 1024 may include output devices such as monitors, touch screen displays, and so on. The toy devices 101 and user devices 102 include at least a processor 1004 and memory 1006, each not pictured for the sake of clarity.

As shown, the memory 1006 contains the interaction application 112, while the storage 1008 contains the user profiles 120, story templates 121, and emoji 122. Generally, the system 1000 is configured to implement all systems, methods, apparatuses, and functionality described above with reference to FIGS. 1-9.

In the foregoing, reference is made to embodiments of the disclosure. However, it should be understood that the disclosure is not limited to specific described embodiments. Instead, any combination of the recited features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the recited aspects, features, embodiments and advantages are merely illustrative and are not considered elements or limitations of the appended claims except where explicitly recited in a claim(s). Likewise, reference to "the disclosure" or "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Embodiments of the disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications or related data available in the cloud. For example, the interaction application 112 could execute on a computing system in the cloud and generate an emoji story for the user. In such a case, the interaction application 112 could store the generated emoji story at a storage location in the cloud. Doing so allows a user to access this information from any computing system attached to a network connected to the cloud (e.g., the Internet).

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the foregoing is directed to embodiments of the present disclosure, other and further embodiments of the disclosure may be devised without departing from the basic scope thereof, and the scope thereof is determined by the claims that follow.

What is claimed is:
1. A method, comprising:
    determining, based on interaction data stored in a first profile, that a first toy device communicated with a second toy device, wherein the first and second toy devices are within a predefined distance during the communication;

determining at least one emotion reflected in an emotion data of the first profile;

determining at least one activity reflected in an activity data of the first profile; and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

2. The method of claim 1, wherein determining the at least one emotion reflected in the emotion data comprises one or more of: (i) analyzing user input from a first user specifying the at least one emotion, (ii) analyzing biometric data of the first user collected by a plurality of biometric sensors to determine the at least one emotion, and (iii) analyzing image data of a captured image of the first user by an emotion detection algorithm to identify the at least one emotion in the captured image of the first user, wherein the first profile is associated with the first user, wherein the story further comprises text indications of the first toy device communicating with the second toy device, the at least one emotion, and the at least one activity.

3. The method of claim 1, further comprising prior to generating the story:

collecting biometric data of a first user by a plurality of biometric sensors, wherein the at least one emotion and the at least one activity are further determined based on the collected biometric data; and selecting the plurality of emoji based on the collected biometric data.

4. The method of claim 3, wherein the at least one activity comprises at least one of a physical activity and a wellness activity reflected in the activity data, the method further comprising:

determining a set of locations visited by the first user, wherein the generated story further comprises an indication of each location in the set of locations visited by the first user.

5. The method of claim 4, further comprising:

computing a physical activity score for the first user based at least in part on: (i) a number of steps walked by the first user and detected by a motion sensor of the first toy device, and (ii) each physical activity engaged in by the first user reflected in the activity data;

computing a wellness score for the first user based at least in part on each wellness activity engaged in by the user;

computing a social interaction score for the first user based on the communication between the first and second toy devices; and computing a travel score for the first user based on the set of locations visited by the user.

6. The method of claim 5, further comprising:

comparing each of the computed scores to a respective threshold; and upon determining one of the computed scores does not exceed the respective threshold, outputting an indication to the first user via a user device of the first user, wherein the indication comprises a recommended activity and a reward, wherein the reward is added to the first profile of the first user upon completion of the recommended activity.

7. The method of claim 1, wherein the story is generated based on a story template, wherein the story template is selected based on at least one preference specified in the first profile, wherein the first and second toy devices communicate via a respective network interface, wherein the plurality of emoji are selected based on the story template and the first profile.

8. A computer program product, comprising:

a non-transitory computer-readable storage medium having computer-readable program code embodied therewith, the computer-readable program code executable by a processor to perform an operation comprising:

determining, based on interaction data stored in a first profile, that a first toy device communicated with a second toy device, wherein the first and second toy devices are within a predefined distance during the communication;

determining at least one emotion reflected in an emotion data of the first profile;

determining at least one activity reflected in an activity data of the first profile; and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

9. The computer program product of claim 8, wherein determining the at least one emotion reflected in the emotion data comprises one or more of: (i) analyzing user input from a first user specifying the at least one emotion, (ii) analyzing biometric data of the first user collected by a plurality of biometric sensors to determine the at least one emotion, and (iii) analyzing image data of a captured image of the first user by an emotion detection algorithm to identify the at least one emotion in the captured image of the first user, wherein the first profile is associated with the first user, wherein the story further comprises text indications of the first toy device communicating with the second toy device, the at least one emotion, and the at least one activity.

10. The computer program product of claim 8, the operation further comprising prior to generating the story:

collecting biometric data of a first user by a plurality of biometric sensors, wherein the at least one emotion and the at least one activity are further determined based on the collected biometric data; and selecting the plurality of emoji based on the collected biometric data.

11. The computer program product of claim 10, wherein the at least one activity comprises at least one of a physical activity and a wellness activity reflected in the activity data, the operation further comprising:

determining a set of locations visited by the first user, wherein the generated story further comprises an indication of each location in the set of locations visited by the first user.

12. The computer program product of claim 11, the operation further comprising:

computing a physical activity score for the first user based at least in part on: (i) a number of steps walked by the first user and detected by a motion sensor of the first toy device, and (ii) each physical activity engaged in by the first user reflected in the activity data;

computing a wellness score for the first user based at least in part on each wellness activity engaged in by the user;

computing a social interaction score for the first user based on the communication between the first and second toy devices; and computing a travel score for the first user based on the set of locations visited by the user.

13. The computer program product of claim 11, the operation further comprising:

comparing each of the computed scores to a respective threshold; and upon determining one of the computed scores does not exceed the respective threshold, outputting an indication to the first user via a user device of the first user, wherein the indication comprises a recommended activity and a reward, wherein the reward is added to the first profile of the first user upon completion of the recommended activity.

14. The computer program product of claim 11, wherein the story is generated based on a story template, wherein the story template is selected based on at least one preference specified in the first profile, wherein the first and second toy devices communicate via a respective network interface, wherein the plurality of emoji are selected based on the story template and the first profile.

15. A system, comprising:

one or more computer processors; and a memory containing a program which when executed by the processors performs an operation comprising:

determining, based on interaction data stored in a first profile, that a first toy device communicated with a second toy device, wherein the first and second toy devices are within a predefined distance during the communication;

determining at least one emotion reflected in an emotion data of the first profile;

determining at least one activity reflected in an activity data of the first profile; and generating, based on the interaction data, the emotion data, and the activity data, a story depicting a plurality of emoji, wherein the plurality of emoji comprise a first emoji reflecting the first toy device communicating with the second toy device, a second emoji reflecting the at least one emotion, and a third emoji reflecting the at least one activity.

16. The system of claim 15, wherein determining the at least one emotion reflected in the emotion data comprises one or more of: (i) analyzing user input from a first user specifying the at least one emotion, (ii) analyzing biometric data of the first user collected by a plurality of biometric sensors to determine the at least one emotion, and (iii) analyzing image data of a captured image of the first user by an emotion detection algorithm to identify the at least one emotion in the captured image of the first user, wherein the first profile is associated with the first user, wherein the story further comprises text indications of the first toy device communicating with the second toy device, the at least one emotion, and the at least one activity.

17. The system of claim 15, the operation further comprising prior to generating the story:

collecting biometric data of a first user by a plurality of biometric sensors, wherein the at least one emotion and the at least one activity are further determined based on the collected biometric data; and selecting the plurality of emoji based on the collected biometric data.

18. The system of claim 17, wherein the at least one activity comprises at least one of a physical activity and a wellness activity reflected in the activity data, the operation further comprising:

determining a set of locations visited by the first user, wherein the generated story further comprises an indication of each location in the set of locations visited by the first user.

19. The system of claim 17, the operation further comprising:

computing a physical activity score for the first user based at least in part on: (i) a number of steps walked by the first user and detected by a motion sensor of the first toy device, and (ii) each physical activity engaged in by the first user reflected in the activity data;

computing a wellness score for the first user based at least in part on each wellness activity engaged in by the user;

computing a social interaction score for the first user based on the communication between the first and second toy devices; and computing a travel score for the first user based on the set of locations visited by the user.

20. The system of claim 17, wherein the story is generated based on a story template, wherein the story template is selected based on at least one preference specified in the first profile, wherein the first and second toy devices communicate via a respective network interface, wherein the plurality of emoji are selected based on the story template and the first profile, the operation further comprising:

comparing each of the computed scores to a respective threshold; and upon determining one of the computed scores does not exceed the respective threshold, outputting an indication to the first user via the system, wherein the indication comprises a recommended activity and a reward, wherein the reward is added to the first profile of the first user upon completion of the recommended activity.

* * * * *